US006776616B2

(12) United States Patent
Dryer

(10) Patent No.: US 6,776,616 B2
(45) Date of Patent: Aug. 17, 2004

(54) VERSATILE SYSTEM FOR MANIPULATION OF DENTAL APPLIANCES

(75) Inventor: Jeffrey Dryer, Allen, TX (US)

(73) Assignee: Dryerpliers, Inc., Plano, TX (US)

( * ) Notice: Subject to any disclaimer, the term of this patent is extended or adjusted under 35 U.S.C. 154(b) by 0 days.

(21) Appl. No.: 10/347,893

(22) Filed: Jan. 20, 2003

(65) Prior Publication Data
US 2003/0224324 A1 Dec. 4, 2003

Related U.S. Application Data

(63) Continuation-in-part of application No. 10/156,596, filed on May 28, 2002, now Pat. No. 6,699,039.

(51) Int. Cl.[7] .................................................. A61C 3/14
(52) U.S. Cl. ..................................................... 433/159
(58) Field of Search ............................... 433/3, 4, 156, 433/153, 155, 159, 40, 141, 146, 162

(56) References Cited

U.S. PATENT DOCUMENTS

| 610,840 | A | * | 9/1898 | Angle |
| 732,288 | A | * | 6/1903 | Felsch |
| 1,487,776 | A | * | 3/1924 | Goldberg |
| 1,518,021 | A | | 11/1924 | Truxillo ........................ 433/159 |
| 1,626,226 | A | * | 4/1927 | Cantor |
| 2,698,483 | A | | 1/1955 | Berkowitz .................... 433/156 |
| 3,713,222 | A | | 1/1973 | Tofflemire .................... 433/159 |
| 4,197,647 | A | | 4/1980 | Goldenthal ................... 433/159 |
| 5,195,889 | A | | 3/1993 | Von Weissenfluh ........... 433/40 |
| 5,839,896 | A | | 11/1998 | Hickok et al. ................ 433/159 |
| 6,095,815 | A | | 8/2000 | Mueller ......................... 433/159 |
| 6,142,781 | A | | 11/2000 | Fischer .......................... 433/149 |
| 6,322,363 | B1 | | 11/2001 | Beecher et al. ............... 433/159 |
| 6,431,864 | B1 | | 8/2002 | Silverstein .................... 433/159 |
| 2002/0016609 | A1 | | 2/2002 | Palemo et al. ................ 433/159 |

OTHER PUBLICATIONS

Matrix Band Forceps advertisement, p. 3 of PracticonDental's Fall 2002 Catalog.
Matrix Band Forceps advertisement, p. 1 of Aug., 2002 Dental Products Report.

* cited by examiner

Primary Examiner—Cary E. O'Connor
(74) Attorney, Agent, or Firm—Ronald W. Burns

(57) ABSTRACT

A versatile system for the manipulation of dental appliances is described that includes a grasping assembly coupled to an actuating assembly. Members of the grasping assembly are shaped to approximate contour of the dental appliance. An apical seating member is disposed upon the grasping assembly to facilitate the application of seating pressure. The grasping assembly may be removably or permanently coupled to the actuating assembly. Portions of the actuating assembly, the grasping assembly, or both the actuating and grasping assemblies may be shaped to facilitate distal, mesial, or both distal and mesial manipulation of the dental appliance.

15 Claims, 6 Drawing Sheets

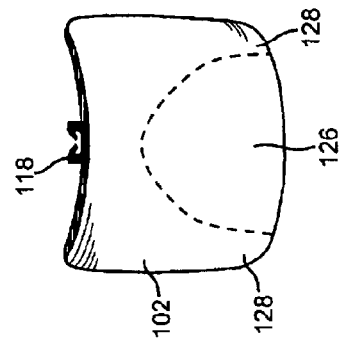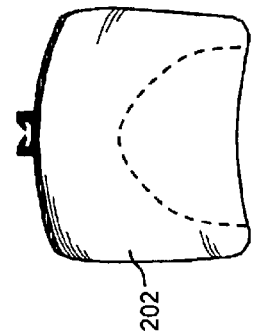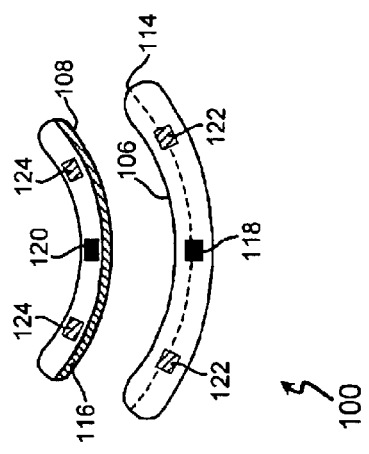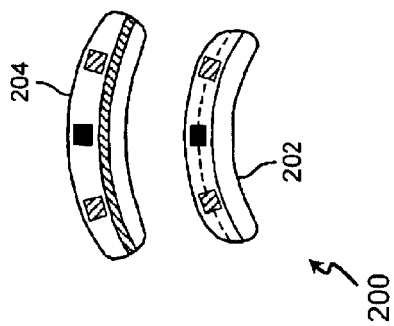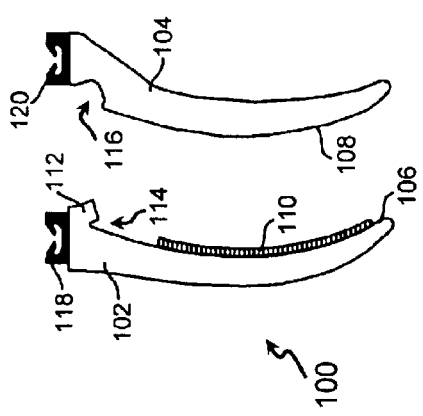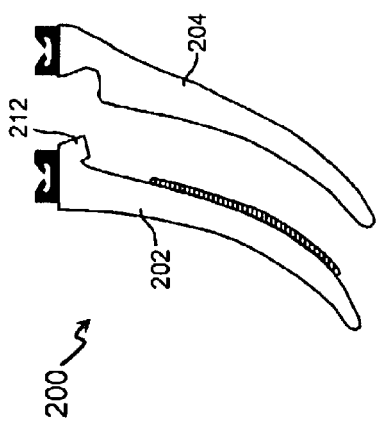

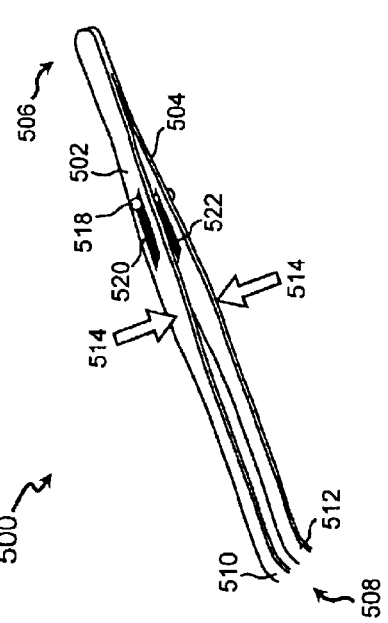
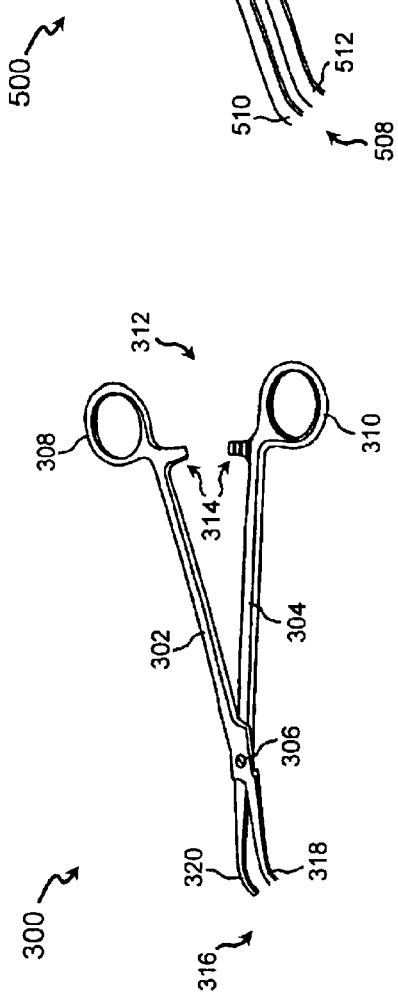
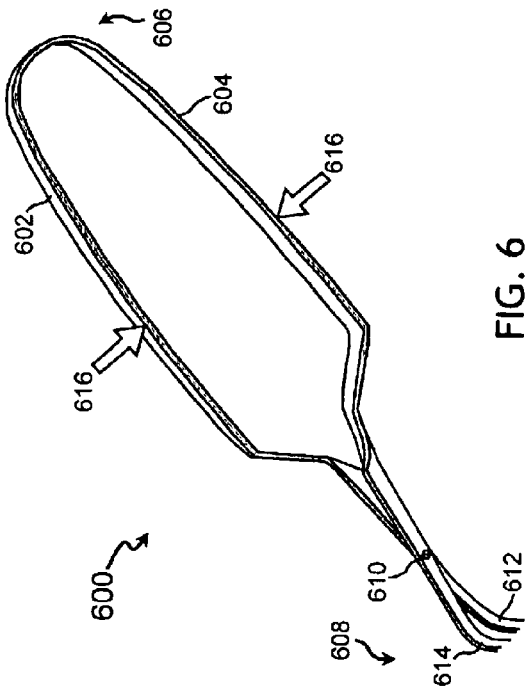
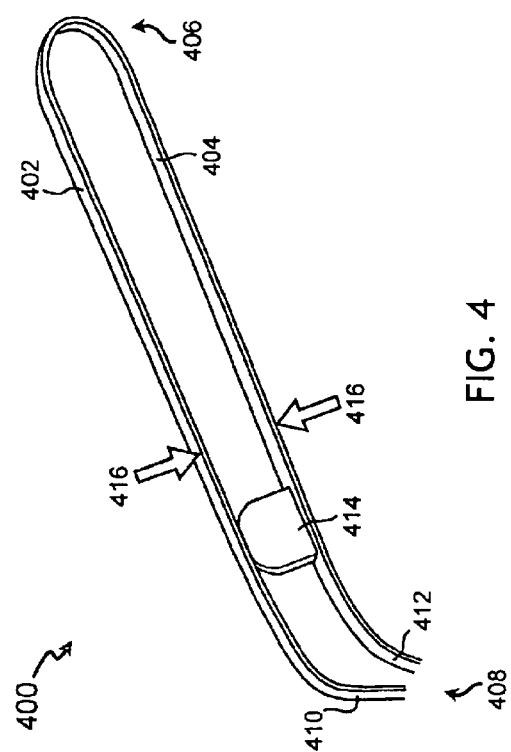

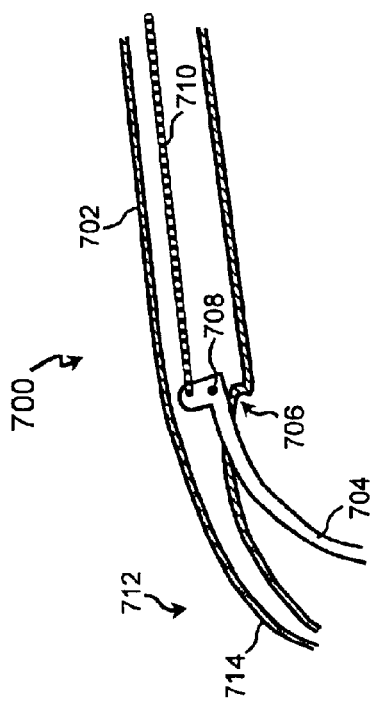
FIG. 7
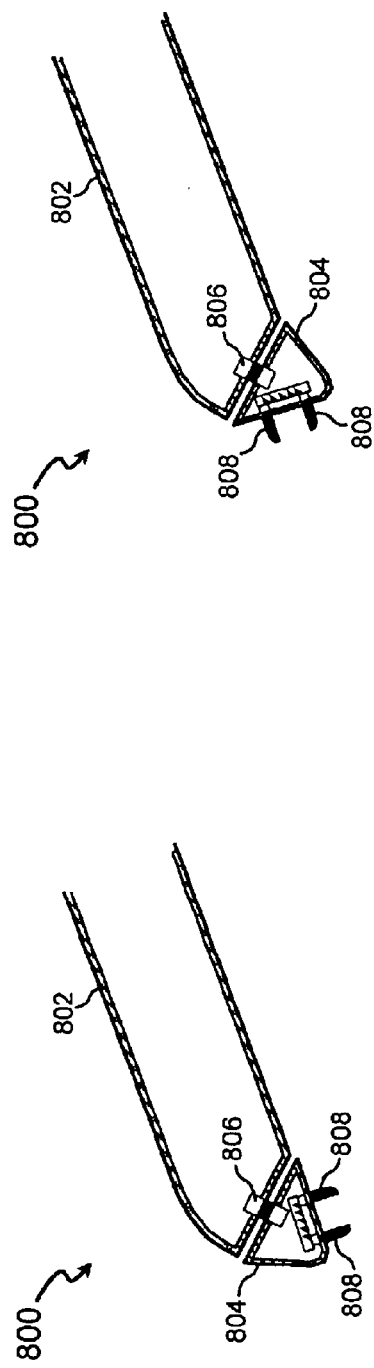
FIG. 8b
FIG. 8a

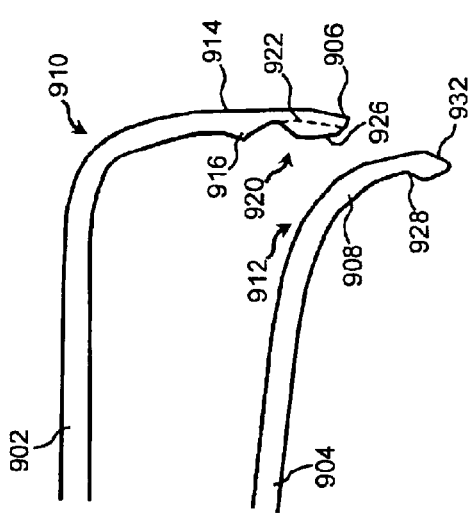
FIG. 9a
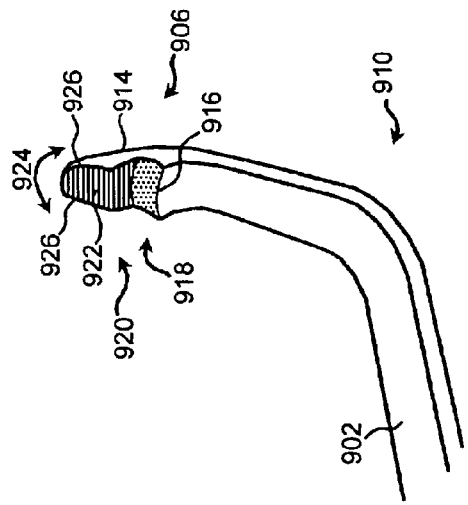
FIG. 9c
FIG. 9b

VERSATILE SYSTEM FOR MANIPULATION OF DENTAL APPLIANCES

CROSS-REFERENCE TO RELATED APPLICATIONS

This patent application is a continuation-in-part of U.S. application Ser. No. 10/156,596, filed on May 28, 2002 now U.S. Pat. No. 6,699,039.

TECHNICAL FIELD OF THE INVENTION

The present invention relates generally to dentistry tools and, more specifically, to a versatile and ergonomic system for manipulation of dental appliances.

BACKGROUND OF THE INVENTION

Dentistry, particularly restorative dentistry, is a demanding craft—requiring a skillful blend of structural engineering and aesthetics. Dentists must artfully construct and shape what are often very complicated restorative structures while working within the confined space of a patient's mouth. Further complicating this already challenging task are safety and sanitary requirements, ergonomic problems, and concerns about patient comfort. At its best, such work might be considered tedious. At its worst, such work might be considered nearly impossible.

As a result, a number of devices and methodologies have been developed to aid dentists in performing routine procedures. Specialized handpieces, powered tools, shielding and grasping devices are continually developed to assist in nearly every aspect of routine dentistry. Often times, however, the development of one aid may simplify a particular aspect of a procedure while complicating other aspects of the same procedure. Furthermore, there are a number of routine procedures, for which no specialized tools exist, that require dentists to utilize existing devices in an unintended fashion. Thus, restorative dentistry often relies on both specialization and improvisation.

Consider, for example, the tools and procedures involved in filling interproximal cavities. Depending upon the location and size of the filling needed, a dentist may have a very difficult time forming a filling of proper structural integrity that provides a desired aesthetic appearance and proper interproximal contact. A relatively popular method of interproximal filling relies on the use of sectional matrix bands.

Sectional matrix bands are small appliances that serve, essentially, as a form for interproximal fillings (especially bonded fillings) when some portion of the external tooth structure is missing or has been removed. The bands are used to restore the tooth structure to its natural contour, without having to dispose excessive bonding material in the area surrounding the filling. These matrix bands are generally formed of aluminum or some other similar semi-rigid material, and typically come in a number of sizes to match tooth and filling sizes. The bands usually have some degree of concavity, in addition to multiple degrees of curvature, to match the often asymmetrical, quasi-spherical contour of a tooth. After proper placement and seating, the matrix bands are usually held in place by some sort of matrix retainer (e.g., a wedge or bi-tine ring).

Thus, once a sectional matrix band is in place, the filling procedure is significantly simplified. The proper placement and seating of a sectional matrix band is, however, no trivial task. It is, in fact, a task that appears to be widely recognized as difficult and involved—and one for which conventional apparatus and methods are not properly adapted.

Conventionally, sectional matrix bands have been placed using only the dentist's fingers, or placed by simple tweezers, straight pliers, or even cotton pliers. These conventional methods share a number of common problems and challenges, and each individual method presents its own unique problems and concerns.

One primary concern is maintaining the integrity of the matrix band itself. Until properly placed, the band is highly susceptible to bending and crimping. This can lead to unacceptable deformities in the band, requiring removal and placement of a new band, or acceptance of a structurally or aesthetically inferior filling.

Even the most nimble of dentists, with the daintiest of fingers, may have difficulty working within the limited space of a patient's mouth to properly place a sectional matrix band without deforming the band. The location of the required filling can further complicate the procedure. The further posterior the required filling is (e.g., between molars), or if the filling is on the mesial surface of a tooth, the more difficult it is to manually place the small, flexible sectional matrix bands. Furthermore, placement by finger may be much more difficult for dentists with larger hands.

Conventional placement methods typically require a great deal of manipulation at ergonomically awkward angles for a dentist. That ergonomically improper manipulation might, over time, lead to degenerative neuromuscular problems. Furthermore, if there is strong interproximal contact between the teeth, the dentist must either ply the teeth apart, such that the instrument used to ply the teeth apart does not impede the placement of the band, or break interproximal contact, in order to place the band without deforming it. Breaking interproximal contact may require removal of an excessive (i.e., unacceptable) amount of tooth structure, however, especially where only a small filling is required.

Although some conventional methods of sectional matrix band placement utilize conventional, general-purpose instruments (e.g., conventional tweezers and pliers)—thereby reducing some of the problems associated with working in the confined space of a patient's mouth—extensive instrument manipulations, ergonomic challenges, and increased potential for damage to the band remain problematic. Using such conventional instruments may still be difficult for posterior placements.

Furthermore, such general-purpose instruments are typically unsuitable for firmly grasping and manipulating the curved sectional matrix bands without deformation. Most such instruments have flat, planar grasping surfaces that can bend or damage a matrix band. The grasping surfaces themselves are generally not arcuate in nature, and thus will not tightly grasp a significant cross section of a sectional matrix band without deformation. Finally, most such conventional instruments are not curved or angled to provide reliable sectional matrix band disposition in both distal and mesial orientations.

More recently, some efforts have been made to redesign or adapt conventional instruments especially for use in sectional matrix band placement. Typically, such adaptations comprise a single, planar angulation or curvature of the grasping end of a simple tweezer or plier-type assembly. Although such adaptations might reduce some of the difficulty in the placement of sectional matrix bands, the full benefit of specialized instruments remains unrealized. For example, conventional instruments typically remain unbiased toward either mesial or distal orientations. Moreover, such instruments typically remain unsuitable for firmly grasping and manipulating the curved sectional matrix bands without deformation. Most such instruments have flat grasping surfaces that are not capable of tightly grasping a significant cross section of a sectional matrix band without deformation.

Thus, sectional matrix band placement is often tedious, time-consuming and, in some cases, not possible using conventional instruments.

SUMMARY OF THE INVENTION

A system that provides easy and reliable placement and removal of specially contoured dental appliances, such as sectional matrix bands, while maintaining the structural and aesthetic integrity of the appliance, readily usable for both distal and mesial manipulations in an ergonomically proper manner, is now needed. This system should provide dentists with a tool that simplifies restorative procedures without deforming or damaging the appliances being placed. The system should thus provide relief from problems associated with conventional methods and apparatus.

Comprehending this, the present invention provides a versatile system for the efficient manipulation of specially contoured dental appliances, especially sectional matrix bands. The present invention provides a contoured grasping member assembly for grasping the dental appliance. The grasping members may be contoured in a variety of topologies and orientations, such that their contour closely approximates the contour of an appliance to be manipulated. Such contouring may be formed in vertical, lateral, or a combination of vertical and lateral, planes using combinations of straight, curved, or angled surfaces. Angulation, curvature, or other deformation may further be employed to facilitate manipulations in distal, mesial, or both mesial and distal orientations.

The present invention also provides an actuating assembly, to which the grasping member assembly may be permanently or temporarily attached, for actuating the grasping member assembly. In the actuating assembly, or in its coupling to the grasping member assembly, angulation, curvature or other deformation may also be employed to facilitate manipulations in distal, mesial, or both mesial and distal orientations. The actuating assembly may be configured such that actuation increases pressure between the grasping members, or configured such that actuation decreases pressure between the grasping members, depending upon the desired orientation and performance characteristics.

The grasping member, or members, on one side of the assembly may include an apical seating feature disposed along an upper edge, to secure the appliance in place and assist in applying seating pressure to the appliance.

Other features and advantages of the present invention will be apparent to those of ordinary skill in the art upon reference to the following detailed description taken in conjunction with the accompanying drawings.

BRIEF DESCRIPTION OF THE DRAWINGS

For a more complete understanding of the present invention, including its features and advantages, reference is made to the following detailed description, taken in conjunction with the following drawing figures. Corresponding numerals and symbols in the different figures refer to corresponding parts unless otherwise indicated:

FIGS. 1a–1c illustrate an embodiment of a grasping member assembly according to the present invention;

FIGS. 2a–2c illustrate another embodiment of a grasping member assembly according to the present invention;

FIG. 3 illustrates an embodiment of an actuating assembly according to the present invention;

FIG. 4 illustrates another embodiment of an actuating assembly according to the present invention;

FIG. 5 illustrates another embodiment of an actuating assembly according to the present invention;

FIG. 6 illustrates another embodiment of an actuating assembly according to the present invention;

FIG. 7 illustrates another embodiment of an actuating assembly according to the present invention;

FIGS. 8a and 8b illustrate another embodiment of an actuating assembly according to the present invention;

FIGS. 9a–9c illustrate another embodiment of an instrument according to the present invention;

DETAILED DESCRIPTION OF THE INVENTION

Figure 10A:
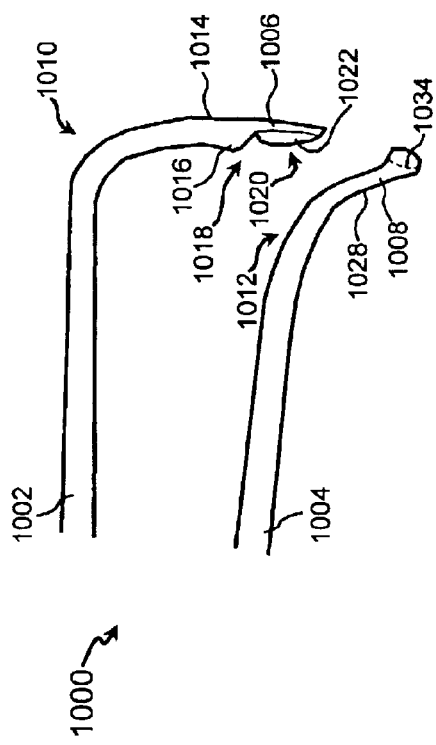
FIGS. 10a–10c illustrate another embodiment of an instrument according to the present invention.

While the making and using of various embodiments of the present invention are discussed in detail below, it should be apparent to those of skill in the art, upon reference to this disclosure, that the system and teachings of the present invention are applicable in a applications. For purposes of explanation and illustration, however, the present invention is hereafter described in reference to the handling and placement of sectional matrix bands for use in an interproximal filling. The principles and teachings disclosed herein, however, are applicable to a wide range of dental instruments and appliances. The specific embodiments discussed herein are thus merely illustrative of specific ways to make and use the invention, and do not limit the scope of the invention.

The present invention defines a system, comprising various structures and methods, for placing and removing matrix bands without excessive manipulation and without deforming or damaging the bands. The present invention provides a contoured grasping member assembly for grasping the dental appliance. The grasping members may be contoured in a variety of topologies and orientations, such that their contour closely approximates the contour of an appliance to be manipulated. Such contouring may be formed in vertical, lateral, or a combination of vertical and lateral, planes using combinations of straight, curved, or angled surfaces. Angulation, curvature, or other deformation may further be employed to facilitate manipulations in distal, mesial, or both mesial and distal orientations. Certain grasping members include an apical seat disposed along an upper edge, and the grasping member assembly may be permanently or temporarily attached to a number of actuating assemblies.

The present invention is now described in greater detail with reference now to FIGS. 1a–1c. FIG. 1a provides a side-view, cross-sectional representation of one embodiment of a grasping member assembly 100 according to the present invention. Assembly 100 comprises first member 102 and second member 104. A sectional matrix band is grasped between surface 106 of member 102 and surface 108 of member 104.

Members 102 and 104 may be formed with a matching convex longitudinal curvature. This curvature can be optimized to match the curvature of one particular size and style of matrix band, or can be generalized to closely approximate the curvatures of a number sizes and styles of matrix bands.

Alternatively, members 102 and 104 may be angled, one or more times, to approximate the desired curvature(s) or, in the alternative, may be formed as substantially straight—without any appreciable curvature or angulation.

Surface 106 may, optionally, incorporate a traction feature 110 (e.g., scoring, small serrations, rubber padding) disposed upon, or embedded within, surface 106. Alternatively, surface 108 may incorporate feature 110. If feature 110 is utilized, it should be formed or disposed so as not to deform the matrix band during contact therewith, and should be made of a material suitable for assembly 100 (suitable materials discussed hereinafter).

Member 102 further comprises an apical seating feature or member 112, usually disposed along the upper perimeter of surface 106. Alternatively, member 112 may be disposed further down along surface 106, or adjustably disposed along surface 106, in order to, for example, facilitate grasping matrix bands of various sizes. Generally, however, feature 112 will be disposed somewhere near the top of member 102. An upper edge of a matrix band is seated against feature 112, to provide stabilization during placement (or removal) and to provide a bearing point for the application of force when placing the band.

As depicted in FIG. 1, member 112 comprises a contiguous appendage along member 102, forming an elongated recess 114 between member 112 and surface 106. Thus, the upper edge of the matrix band would seat within recess 114 while held by assembly 100.

Alternatively, feature 112 may comprise an intermittent series of short appendages forming similar recesses. In other alternatives feature 112 may comprise one or more simple flat shelves, or one or more post or semi-spherical protuberances, disposed or formed in a flush relation with surface 106 (i.e., without recess 114) to provide the required stabilization and bearing point(s). In further alternative embodiments, feature 112 may be formed in similar fashion along member 104.

In the embodiment depicted in FIGS. 1a–1c, however, member 112 is disposed along the outermost member of assembly 100 because of the curvature of members 102 and 104. Thus, the member farthest from the tooth being filled applies bearing pressure. Member 104 may be formed with a deviation 116 to receive or accommodate member 112 while members 102 and 104 are brought together. Surface 108 is formed of a longitudinal size comparable to, but somewhat smaller than, surface 106 to allow for clearance of seating member 112 when members 102 and 104 are closed tightly together.

Members 102 and 104 further comprise attachment features (or members) 118 and 120, respectively, disposed along the upper portions thereof. Depending upon the desired actuating assembly to which members 102 and 104 will be coupled, and upon whether such coupling is intended to be permanent or temporary (i.e., removable), features 118 and 120 may be implemented in a number of ways.

For example, if attachment is intended to be removable, members 118 and 120 may comprise a snap-lock or screw-on mechanism. If attachment is intended to be permanent, members 118 and 120 may comprise welds, or some or similar adjoinment, to an actuating member. Alternatively, members 102 and 104 may be formed as a contiguous, integral part of an actuating assembly, such that members 118 and 120 comprise only a transition area indistinguishable from surrounding structure.

Referring now to FIG. 1b, a top view representation of assembly 100 is depicted. Members 102 and 104 may be additionally formed with a matching convex lateral curvature. This curvature can be optimized to match the curvature of one particular size and style of sectional matrix band, or can be generalized to closely approximate the curvatures of a number sizes and styles of matrix bands. Alternatively, once again, the same effect may be achieved using one or more angulations. In the alternative, curvature or angulation may be omitted altogether—leaving, in the lateral direction, a substantially planar surface.

Although depicted in FIG. 1b as laterally larger, member 102 may be laterally larger, similar, or smaller than member 104, depending upon the desired support and manipulation characteristics of assembly 100.

Furthermore, depending upon the desired actuating assembly and the relative sizes, members 102 and 104 may comprise multiple lateral attachment members 122 and 124, respectively, in addition to or instead of members 118 and 120. Members 122 and 124 are disposed or formed so as to provide greater lateral stability across the breadth of members 102 and 104, if those members comprise a single piece. If members 102 and 104 themselves comprise multiple sub-members, then members 122 and 124 may provide individual attachment for each of the sub-members.

As illustrated in FIG. 1c, in a front-view representation, member 102 may comprise a single, contiguous structure. Alternatively, one or more partial aperture(s) 126 may be formed in member 102 so as to render multiple tines 128 in the lower portion of member 102. Another alternative embodiment would render member 102 as set of multiple, physically separated, polygonal or tine sub-members formed or disposed in accordance with the teachings above. All such embodiments provide a broader base of contact with the sectional matrix band than conventional instruments (e.g., cotton pliers)—enabling a dentist to apply rotational force along the horizontal axes of the band. Although not depicted, all of these variations may also be implemented with member 104. Furthermore, members 102 and 104 can be formed to have matching implementations, or differing combinations of the above-referenced embodiments.

Another embodiment of the present invention is now described with reference to FIGS. 2a–2c. FIG. 2a provides a side-view, cross-sectional representation of a grasping member assembly 200 according to the present invention. Assembly 200 and its constituent members are essentially identical to assembly 100 and its members, with the exception of curvatures (or angulations) and related orientation considerations. Members 202 and 204, which correspond to members 102 and 104, respectively, are formed with a matching concave longitudinal curvature. Again, this curvature can be: optimized to match the curvature of one particular size and style of sectional matrix band; generalized to closely approximate the curvatures of a number of sizes and styles of matrix bands; or omitted altogether. Apical seating feature 212 is disposed along member 202, which is the innermost member of assembly 200. Thus, in this embodiment, the member closest to the tooth being filled applies bearing pressure. In alternative embodiments, apical seating feature 212 may be disposed along member 204.

Referring now to FIG. 2b, a top view representation of assembly 200 is depicted. Members 202 and 204 are additionally formed with a matching concave lateral curvature. Again, this curvature can be: optimized to match the curvature of one particular size and style of sectional matrix band; generalized to closely approximate the curvatures of a number of sizes and styles of matrix bands; or omitted altogether. Although depicted as laterally smaller, member 202 may be laterally larger, similar, or smaller than member 204, depending upon the desired support and manipulation characteristics of assembly 200.

As illustrated in FIG. 2c, member 202 may comprise a single contiguous structure, a tined structured, or multiple sub-member structures (not depicted). Again, all of these embodiments are also possible with member 204, and members 202 and 204 can be formed to have matching implementations, or differing combinations of the above-referenced embodiments.

Although assemblies 100 and 200 have been depicted and described as comprising multiple members, other embodiments thereof may comprise only a single member. For example, it is possible that only member 102 of assembly 100 may be disposed upon some simple actuating member (e.g., a handpiece). While such an embodiment would still provide advantages over conventional methods and apparatus, it would not provide the dentist with the same ability to secure (i.e., by grasping) a sectional matrix band for manipulation and proper placement as the multiple member embodiments do.

With the exception of the single member embodiment above, the grasping member assemblies 100 and 200 of the present invention should be coupled to, or formed as part of, some compound actuating assembly. According to the present invention, a compound actuating assembly may comprise either a bifurcated assembly (e.g., tweezers, forceps, pliers), or a stylus assembly (e.g., specialized handpiece, pneumatic drill piece), adapted to meet the requirements of the present invention. Although an almost limitless range of actuating assembly implementations are possible, the present invention requires that an actuating assembly be of a profile and length that allows adequate access to all teeth for the grasping assembly without requiring excessive manipulation by the dentist. The actuating assembly should provide sufficient pressure between the members of the grasping assembly to securely hold a matrix band. Preferably, the actuating assembly should provide the dentist with the ability to selectively adjust the grasping pressure applied.

Referring now to FIG. 3, assembly 300 illustrates one embodiment of a bifurcated actuating assembly according to the present invention. Assembly 300 comprises first body member 302 and second body member 304, counter-rotationally coupled together about hinge 306. As depicted, assembly 300 comprises a scissor-style forceps assembly, having finger retainers 308 and 310 coupled to members 302 and 304, respectively, at handling end 312 of the assembly. End 312 is the end of assembly 300 that a dentist will grasp while using and manipulating it. Alternatively, members 302 and 304 may just have flat, unfinished terminations at end 312, or may have some other devices disposed in place of retainers 308 and 310 to provide grasping assistance (e.g., scored surfaces, rubber pads). Optionally, assembly 300 may further comprise a locking assembly 314 to, at a minimum, secure closure of assembly 300 and, further optionally, to provide a progression of locking pressures. As depicted in FIG. 3, assembly 314 comprises two counterposed, ratcheting hasps disposed upon members 302 and 304 that lock together progressively tighter as closing pressure is applied to members 302 and 304, and release from one another when a slight orthogonal force is applied thereto. Alternatively, assembly 314 may comprise a simple latch, a screw-type apparatus, a spring apparatus, or any other contrivance that provides the desired locking and pressure characteristics.

The other end of assembly 300 is actuating end 316. At end 316, members 302 and 304 terminate in actuating portions 318 and 320, respectively. Members of a grasping assembly may couple to, or be formed as part of, the open ends of portions 318 and 320. Portions 318 and 320 are angled or curved with respect to members 302 and 304 to provide an attached grasping assembly proper access to either distal or mesial surfaces, or both. The angles or curvatures of portions 318 and 320 are matched and aligned to provide proper closure and alignment of grasping assembly members. The curvature or angling of portions 318 and 320 enables a dentist to place a sectional matrix band in the desired location without manipulating the entire actuating assembly to some extreme angle within a patient's mouth. Depending on whether the coupling of grasping assembly members to portions 318 and 320 is permanent or temporary, and on whether assembly 300 is intended to be used for only mesial, only distal, or both mesial and distal orientations, portions 318 and 320 may be formed with a specific or a general curvature or angling. Alternatively, where the grasping assembly members themselves are angled or curved to facilitate a particular orientation, portions 318 and 320 may be formed substantially straight.

By way of illustration, separate tools for mesial and distal orientations might be desired. Thus, two actuating assemblies would be formed. Each may have grasping assemblies permanently attached thereto. The tool intended for use in mesial orientations may comprise actuating portions having a greater degree of curvature or angling than the actuating portions of the tool intended for distal orientations—effecting more efficient and less manipulation-intensive placements of both the mesial and distal oriented appliances.

Alternatively, a single tool for use in either orientation may be desired. Such a tool might have actuating portions of a generalized curvature or angle, and might rely on temporary attachment of, for example, grasping assembly 100 for mesial orientation and grasping assembly 200 for distal orientation. In still another alternative embodiment, a tool may comprise actuating portions of adjustable or deformable curvature or angling, allowing a dentist to select his own orientation based on the procedure to be completed.

Finally, hinge 306 may be disposed along members 302 and 304 in a position generally biased toward end 316. This renders members 302 and 304 as relatively long lever arms, requiring minimal application of force and minimal separation of members 302 and 304 at end 312 to provide sufficient actuation of portions 318 and 320.

Referring now to FIG. 4, another embodiment of a bifurcated actuating assembly 400 is illustrated. Assembly 400 comprises first body member 402 and second body member 404, conjoined together as a single unit at closed end 406. The other end of assembly 400 is actuating end 408. At end 408, members 402 and 404 terminate in actuating portions 410 and 412, respectively. Members of a grasping assembly may be coupled to, or formed as part of, the open ends of portions 410 and 412.

As depicted, assembly 400 comprises a specialized tweezer-style assembly—one that brings actuating portions 410 and 412, and grasping assembly members coupled thereto, together at rest. Assembly 400 comprises a fulcrum member 414 disposed between members 402 and 404. Member 414 is disposed is a position biased towards end 408, and portions 410 and 412 are formed, such that grasping assembly members coupled to portions 410 and 412 are brought together and engaged (i.e., clamped) with maximum force when assembly 400 is not actuated. Assembly 400 is actuated by applying pressure to areas 416 along members 402 and 404, between fulcrum 414 and end 406—separating portions 410 and 412 and releasing the grasp of the grasping assembly.

Optionally, members 402 and 404 may have some devices disposed thereon, proximal to end 406, to provide grasping assistance (e.g., scored surfaces, rubber pads). Furthermore, assembly 400 may optionally comprise a locking assembly (not depicted) to, at a minimum, secure the resting closure of assembly 400. The locking assembly may comprise a latch, a hasp, a spring apparatus, or any other contrivance that provides the desired locking characteristic.

At end 408, the grasping assembly members may couple to, or be formed as part of, the open ends of portions 410 and 412. Portions 410 and 412 are angled or curved with respect to members 402 and 404 to provide an attached grasping assembly proper access to either distal or mesial surfaces, or both. The angles or curvatures of portions 410 and 412 are matched and aligned to provide proper closure and alignment of grasping assembly members. Again, the curvature or angling of portions 410 and 412 enables a dentist to place a matrix band in the desired location without manipulating the entire actuating assembly to some extreme angle within a patient's mouth. Depending on whether the coupling of grasping assembly members to portions 410 and 412 is permanent or temporary, and on whether assembly 400 is intended to be used for only mesial, only distal, or both mesial and distal orientations, portions 410 and 412 may be formed with a specific or a general curvature or angling or may, in the alternative, be substantially straight.

In one embodiment, for example, separate tools for mesial and distal orientations might be desired. Thus, two actuating assemblies are formed. Each may have grasping assemblies permanently attached thereto. The tool intended for use in mesial orientations would comprise actuating portions having a greater degree of curvature or angling than the actuating portions of the tool intended for distal orientations—effecting more efficient and less manipulation-intensive placements of both the mesial and distal oriented appliances.

Alternatively, a single tool for use in either orientation may be desired. Such a tool might have actuating portions of a generalized curvature or angle, and might rely on temporary attachment of, for example, grasping assembly 100 for mesial orientation and grasping assembly 200 for distal orientation. In still another alternative embodiment, a tool may comprise actuating portions of adjustable or deformable curvature or angling, allowing a dentist to select his own orientation based on the procedure to be completed.

Referring now to FIG. 5, another embodiment of a bifurcated actuating assembly 500 is illustrated. Assembly 500 comprises first body member 502 and second body member 504, joined together as a single unit at closed end 506. The other end of assembly 500 is actuating end 508. At end 508, members 502 and 504 terminate in actuating portions 510 and 512, respectively. Members of a grasping assembly may be coupled to, or formed as part of, the open ends of portions 510 and 512.

As depicted, end 506 of assembly 500 comprises a conventional tweezer-style assembly—one that requires the application of closing pressure 514 somewhere along members 502 and 504 in order to bring actuating portions 510 and 512, and grasping assembly members coupled thereto, together. Thus, grasping assembly members coupled to portions 510 and 512 are brought together and engaged (i.e., clamped) with increasing force as the pressure 514 applied to assembly 500 is increased. Removing pressure 514 from assembly 500 separates portions 510 and 512 and releases the grasp of the grasping assembly. Optionally, members 502 and 504 may have some devices disposed thereon, proximal to end 506, to provide grasping assistance (e.g., scored surfaces, rubber pads).

Furthermore, assembly 500 may optionally comprise a locking assembly 516 to, at a minimum, secure closure of assembly 500 and, further optionally, to provide a progressive locking pressure. As depicted in FIG. 5, assembly 516 comprises a sliding bar member 518 disposed within apertures 520 and 522, themselves disposed within members 502 and 504, respectively. Sliding member 518 may be positioned and anchored within apertures 520 and 522 such that as it moved in the direction of end 508, members 502 and 504 are forced closer together—providing or matching pressure 514. Thus, a dentist may lock assembly 500 at a desired grasping pressure after applying closing pressure directly to members 502 and 504, or assembly 516 may be used to indirectly close assembly 500 to a desired grasping pressure before locking it in place. Pressure between grasping assembly members may be increased by moving member 518 further in the direction of end 508. Alternatively, assembly 516 may comprise a thumbwheel-type assembly that enables a dentist to indirectly close, lock, and increase the grasping pressure for, assembly 500 by turning the thumbwheel. In other embodiments, assembly 516 may comprise a simple latch, a screw-type apparatus, a spring apparatus, or any other contrivance that provides the desired locking and pressure characteristics.

At end 508, the grasping assembly members may be coupled to, or formed as part of, the open ends of portions 510 and 512. Portions 510 and 512 are angled or curved with respect to members 502 and 504 to provide an attached grasping assembly proper access to either distal or mesial surfaces, or both. The angles or curvatures of portions 510 and 512 are matched and aligned to provide proper closure and alignment of grasping assembly members. Again, the curvature or angling of portions 510 and 512 enables a dentist to place a sectional matrix band in the desired location without manipulating the entire actuating assembly to some extreme angle within a patient's mouth. Depending on whether the coupling of grasping assembly members to portions 510 and 512 is permanent or temporary, and on whether assembly 500 is intended to be used for only mesial, only distal, or both mesial and distal orientations, portions 510 and 512 may be formed with a specific or a general curvature or angling or may, in the alternative, be substantially straight.

In one embodiment, for example, separate tools for mesial and distal orientations might be desired. Thus, two actuating assemblies are formed. Each may have grasping assemblies permanently attached thereto. The tool intended for use in mesial orientations would comprise actuating portions having a greater degree of curvature or angling than the actuating portions of the tool intended for distal orientations—effecting more efficient and less manipulation-intensive placements of both the mesial and distal oriented appliances.

Alternatively, a single tool for use in either orientation may be desired. Such a tool might have actuating portions of a generalized curvature or angle, and rely on temporary attachment of, for example, grasping assembly 100 for mesial orientation and grasping assembly 200 for distal orientation. In still another alternative embodiment, a tool may comprise actuating portions of adjustable or deformable curvature or angling, allowing a dentist to select his own orientation based on the procedure to be completed.

Referring now to FIG. 6, assembly 600 illustrates another embodiment of a bifurcated actuating assembly according to the present invention. Assembly 600 comprises first body member 602 and second body member 604, conjoined together as a single unit at closed end 606. The other end of assembly 600 is actuating end 608. Assembly 600 further comprises hinge 610, disposed along members 602 and 604 proximal to end 608, and about which members 602 and 604 are counter-rotationally coupled together. At end 608, members 602 and 604 terminate in actuating portions 612 and 614, respectively. Members of a grasping assembly may be coupled to, or formed as part of, the open ends of portions 612 and 614.

As depicted, assembly 600 comprises a specialized scissor-style assembly—one that brings actuating portions 612 and 614, and grasping assembly members coupled thereto, together at rest. Assembly 600 is configured, and portions 612 and 614 are formed, such that grasping assembly members coupled to portions 612 and 614 are brought together and engaged (i.e., clamped) with maximum force when assembly 600 is not actuated. Assembly 600 is actuated by applying pressure to areas 616 along members 602 and 604, between hinge 610 and end 606—separating portions 612 and 614 and releasing the grasp of the grasping assembly.

Optionally, members 602 and 604 may have some devices disposed thereon, proximal to end 606, to provide grasping assistance (e.g., scored surfaces, rubber pads). Furthermore, assembly 600 may optionally comprise a locking assembly (not depicted) to, at a minimum, secure the resting closure of assembly 600. The locking assembly may comprise a latch, a hasp, a spring apparatus, or any other contrivance that provides the desired locking characteristic.

At end 608, the grasping assembly members may couple to, or be formed as part of, the open ends of portions 612 and 614. Portions 612 and 614 are angled or curved with respect to members 602 and 604 to provide an attached grasping assembly proper access to either distal or mesial surfaces, or both. The angles or curvatures of portions 612 and 614 are matched and aligned to provide proper closure and alignment of grasping assembly members. Again, the curvature or angling of portions 612 and 614 enables a dentist to place a sectional matrix band in the desired location without manipulating the entire actuating assembly to some extreme angle within a patient's mouth. Depending on whether the coupling of grasping assembly members to portions 612 and 614 is permanent or temporary, and on whether assembly 600 is intended to be used for only mesial, only distal, or both mesial and distal orientations, portions 612 and 614 may be formed with a specific or a general curvature or angling or may, in the alternative, be substantially straight.

In one embodiment, for example, separate tools for mesial and distal orientations might be desired. Thus, two actuating assemblies are formed. Each may have grasping assemblies permanently attached thereto. The tool intended for use in mesial orientations would comprise actuating portions having a greater degree of curvature or angling than the actuating portions of the tool intended for distal orientations—effecting more efficient and less manipulation-intensive placements of both the mesial and distal oriented appliances.

Alternatively, a single tool for use in either orientation may be desired. Such a tool might have actuating portions of a generalized curvature or angle, and might rely on temporary attachment of, for example, grasping assembly 100 for mesial orientation and grasping assembly 200 for distal orientation. In still another alternative embodiment, a tool may comprise actuating portions of adjustable or deformable curvature or angling, allowing a dentist to select his own orientation based on the procedure to be completed.

As an alternative to the bifurcated assemblies described above, the compound actuating assembly of the present invention may be implemented in a variety of stylus-type embodiments. Referring now to FIG. 7, assembly 700 illustrates one embodiment of a stylus actuating assembly according to the present invention. Assembly 700 comprises a first body member 702 and second body member 704. Member 704 may be coupled, either internally or externally, to member 702, within a recessed portion 706 of member 702 by a hinge assembly 708. A closure mechanism 710 within member 702 is operatively associated with member 704.

Member 704 is coupled to member 702 close to actuating end 712 of assembly 700. At end 712, member 702 terminates in actuating portion 714. Members of a grasping assembly may be coupled to, or formed as part of, the open ends of member 704 and portion 714.

As depicted, activation of mechanism 710 will cause member 704 to rotate about hinge 708, bringing actuating portion 714 and member 704, and grasping assembly members coupled thereto, together. Thus, grasping assembly members coupled to portion 714 and member 704 are brought together and engaged (i.e., clamped) with increasing force as the force applied by mechanism 710 is increased. Mechanism 710 may comprise a simple, finger-activated, mechanical trigger assembly, an electromechanical solenoid, a pneumatically activated solenoid, or any other similar contrivance enabling a dentist to apply a fixed or progressive range of closing pressures to member 704. Removing or reversing the closing pressure applied to member 704 will separate member 704 from portion 714, releasing the grasp of the grasping assembly. Assembly 700 may, optionally, comprise a locking apparatus or assembly of the types previously described, such that mechanism 710, member 704, or both may be locked into a desired position.

At end 712, grasping assembly members may couple to, or be formed as part of, the open ends of portion 714 and member 704. Portion 714 and member 704 are angled or curved with respect to member 702 to provide an attached grasping assembly proper access to either distal or mesial surfaces, or both. The angles or curvatures of portion 714 and member 704 are matched and aligned to provide proper closure and alignment of grasping assembly members. Again, the curvature or angling of portion 714 and member 704 enables a dentist to place a sectional matrix band in the desired location without manipulating the entire actuating assembly to some extreme angle within a patient's mouth. Depending on whether the coupling of grasping assembly members to portion 714 and member 704 is permanent or temporary, and on whether assembly 700 is intended) to be used for only mesial, only distal, or both mesial and distal orientations, portion 714 and member 704 may be formed with a specific or a general curvature or angling. Again, an alternative embodiment may comprise a substantially straight portion 714 and member 704 where the grasping assembly members are formed with sufficient angling or curvature to facilitate either a mesial or distal orientation.

As an illustration, separate tools for mesial and distal orientations might be desired. Thus, two actuating assemblies would be formed. Each may have grasping assemblies permanently attached thereto. The tool intended for use in mesial orientations would comprise portion 714 and member 704 having a greater degree of curvature or angling than portion 714 and member 704 of the tool intended for distal orientations—effecting more efficient and less manipulation-intensive placements of both the mesial and distal oriented appliances.

Alternatively, a single tool for use in either orientation may be desired. Such a tool might have portion 714 and member 704 of a generalized curvature or angle, and might rely on temporary attachment of, for example, grasping assembly 100 for mesial orientation and grasping assembly 200 for distal orientation. In still another alternative embodiment, a tool may comprise portion 714 and member 704 of adjustable or deformable curvature or angling, allowing a dentist to select his own orientation based on the procedure to be completed.

Referring now to FIG. 8a, another embodiment of a stylus assembly 800 is illustrated. Assembly 800 comprises a first body member 802 and second body member 804. Members 802 and 804 are inter-connectively coupled together by intermediary member 806. Actuating members 808 are disposed upon or within member 804, and are adapted to couple with and actuate members of a grasping assembly (not shown). Members of a grasping assembly may be coupled to, or formed as part of, the open ends of members 808. Member 806 may provide a conduit from member 802 to member 804 through which a closure mechanism (not shown) may be operatively coupled to members 808. Such a closure mechanism may comprise any suitable mechanical, electromechanical, or pneumatic contrivance (e.g., pneumatic solenoid) operable to allow a dentist, while handling member 802, to engage and disengage members 808 as desired. Thus, grasping assembly members coupled to members 808 are brought together and engaged (i.e., clamped) with increasing force as the force applied by the closure mechanism is increased. Removing or reversing the force applied will separate members 808, releasing the grasp of the grasping assembly.

In addition to, or as an alternative to, serving as a conduit, member 806 may serve as a pivot, about which member 804 may be rotated or otherwise translated, with respect to member 802, to provide an attached grasping assembly proper access to either distal or mesial surfaces, or both. This is illustrated in FIG. 8b, where the rotation of member 804 changes the angle of members 808 with respect to member 802. In this example, the orientation of FIG. 8a might be preferable for mesial procedures and the orientation of FIG. 8b might be preferable for distal procedures. Alternatively, or in addition to its rotation, member 804 may be formed with an asymmetry (e.g., quasi-pyramidal or quasi-spherical) such that the rotation of member 804 further enhances bias of assembly 800 to either distal or mesial orientations. In other alternative embodiments, certain members (e.g., member 806) may be adjustable or deformable with respect to other members to achieve the desired effect. In still other alternative embodiments, multiple rotational and pivotal members of parallel and orthogonal orientation may be utilized to render the desired result. All such embodiments are configured to enable a dentist to place a sectional matrix band in a desired location without manipulating the entire actuating assembly to some extreme angle within a patient's mouth.

Referring now to FIGS. 9a–9c, a portion of an assembled instrument 900 according to the present invention is illustrated. Instrument 900 comprises a first actuating member 902 and a second actuating member 904. Although not shown in FIG. 9a, members 902 and 904 are joined together as a single unit at closed end, in a configuration similar to assembly 500 of FIG. 5. In the alternative, other actuating assemblies in accordance with the present invention may be utilized.

Respectively coupled to, or formed as part of, members 902 and 904 are grasping members 906 and 908. Transition areas 910 and 912 comprise the regions of co-formation or attachment between members 902 and 906, and members 904 and 908, respectively.

Depending upon the configuration of, and the temporary or permanent nature of the connection between, the actuating and grasping assemblies used, transition areas 910 and 912 may be considered part of members 902 and 904, respectively, or part of members 906 and 908, respectively, or both. Areas 910 and 912 are angled or curved to facilitate a distal orientation in accordance with present invention, and are aligned to provide proper engagement of members 906 and 908 as described hereafter.

Member 906 is formed having an outer surface 914 and various inner surface features. Along its inner surface, member 906 comprises an apical seating feature 916. Feature 916 may comprise a ridge, shelf or other contrivance in accordance with the present invention. Feature 916 may protrude slightly from the inner surface of member 916, or may be flush or contoured therewith. Member 906 further comprises a recessed area 918, formed adjoined to feature 916.

Depending upon the specific configuration of member 906, and of feature 916, area 918 may be formed as either a straight or curved, single or multi-faceted surface providing access and clearance for engagement between a sectional matrix band and feature 916. Area 918 may form a well-defined edge along feature 916, a smooth, rounded edge, or any other suitable transition.

Member 906 terminates with grasping area 920, which adjoins area 918. Grasping area 920 is formed with a grasping surface 922 having a concave lateral curvature axis 924. Grasping surface 922 terminates in outer lateral edges 926. The lateral curvature of surface 922 is formed, in accordance with the present invention, to match or closely approximate the curvature of a sectional matrix band or other desired dental appliance. In alternative embodiments, angulations may be implemented in place of curvature or curvature may be omitted altogether.

As depicted in FIGS. 9a–9c, surface 922 further comprises some longitudinal curvature, orthogonal to axis 924, to match or closely approximate the curvature of a sectional matrix band or other desired dental appliance. In other embodiments, the longitudinal axis of surface 922 may be substantially straight, or may comprise some angulation to match or closely approximate the curvature of a sectional matrix band or other desired dental appliance. Thus, surface 922 may be formed in resemblance to a number of contour profiles (e.g., quasi-spherical, egg-shaped, quasi-conical, quasi-cylindrical, etc.).

Member 908 is formed having an outer surface 928 and various inner surface features. Along its inner surface, member 908 comprises a mating feature 930 and a grasping surface 932. Feature 930 is formed, in accordance with the present invention, to provide secure engagement in cooperation with feature 916 as described in greater detail hereafter. Feature 930 may comprise a ridge, shelf or other contrivance, and provides a transition from, and demarcation between, region 912 and surface 932.

Grasping surface 932 has a convex lateral curvature, formed to complement the curvature axis 924 of surface 922, in accordance with the present invention. The lateral curvature of surface 932 is formed, in accordance with the present invention, to match or closely approximate the curvature of a sectional matrix band or other desired dental appliance. In alternative embodiments, angulations may be implemented in place of curvature or curvature may be omitted altogether.

As depicted in FIGS. 9a–9c, surface 932 further comprises some longitudinal curvature, to match or closely approximate the curvature of a sectional matrix band or other desired dental appliance. In other embodiments, the longitudinal axis of surface 932 may be substantially straight, or may comprise some angulation in accordance with the present invention.

Although the specific embodiments of constituent members may vary slightly, apparatus 900 is generally formed and operable to render members 906 and 908 in pressure-fit, engagable relation to one another while grasping a sectional matrix band between surfaces 922 and 932. The orientations, curvatures, or angulations of members 902, 904, 906, 908, 910, 912, 916, 918, 920, 922, 926, 930, and 932 are, in this embodiment, formed to facilitate the placement or manipulation of a sectional matrix band in a distal orientation. As actuating members 902 and 904 are brought together, grasping area 920 is brought down into a partially sleeved relationship over feature 930 and surface 932. Depending upon a user's preference, a sectional matrix band may be positioned in instrument 900 prior to, or just as, area 920 initiates contact with member 908.

As further pressure is applied to members 902 and 904, feature 930 slides longitudinally along surface 922 until it enters recess 918 and comes to rest against feature 916. Surfaces 922 and 932 thus come into pressure fit contact with one another, holding the sectional matrix band stably and securely therebetween. The matrix band is further stabilized and secured, along its upper edge, against feature 916.

In alternative embodiments, increased grasping pressure may be induced between members 906 and 908 utilizing some locking or fulcrum mechanism in accordance with the present invention, as previously described.

Figure 10C:
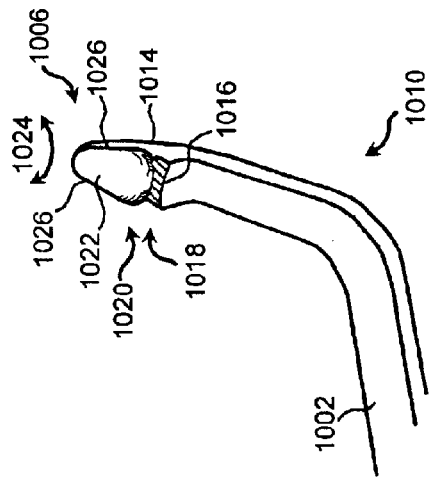
Figure 10B:
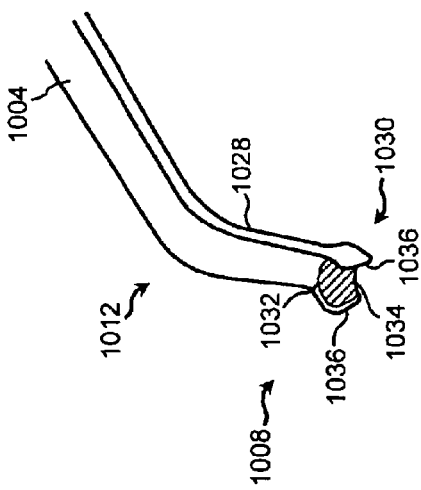

Referring now to FIGS. 10a–10c, a portion of an assembled instrument 1000 according to the present invention is illustrated. Instrument 1000 comprises a first actuating member 1002 and a second actuating member 1004. Although not shown in FIG. 10a, members 1002 and 1004 are joined together as a single unit at closed end, in a configuration similar to assembly 500 of FIG. 5. In the alternative, other actuating assemblies in accordance with the present invention may be utilized.

Respectively coupled to, or formed as part of, members 1002 and 1004 are grasping members 1006 and 1008. Transition areas 1010 and 1012 comprise the regions of co-formation or attachment between members 1002 and 1006, and members 1004 and 1008, respectively.

Depending upon the configuration of, and the temporary or permanent nature of the connection between, the actuating and grasping assemblies used, transition areas 1010 and 1012 may be considered part of members 1002 and 1004, respectively, or part of members 1006 and 1008, respectively, or both. Areas 1010 and 1012 are angled or curved to facilitate a mesial orientation in accordance with present invention, and are aligned to provide proper engagement of members 1006 and 1008 as described hereafter.

Member 1006 is formed having an outer surface 1014 and various inner surface features. Along its inner surface, member 1006 comprises an apical seating feature 1016. Feature 1016 may comprise a ridge, shelf or other contrivance in accordance with the present invention. Feature 1016 may protrude slightly from the inner surface of member 1016, or may be flush or contoured therewith. Member 1006 further comprises a recessed area 1018, formed adjoined to feature 1016. In alternative embodiments, member 1016 may be similarly formed or disposed along the inner surface of member 1008, as described hereafter in reference to FIG. 11.

Depending upon the specific configuration of member 1006, and of feature 1016, area 1018 may be formed as either a straight or curved, single or multi-faceted surface providing access and clearance for engagement between a sectional matrix band and feature 1016. Area 1018 may form a well-defined edge along feature 1016, a smooth rounded edge, or any other suitable transition.

Member 1006 terminates with grasping area 1020, which adjoins area 1018. Grasping area 1020 is formed with a grasping surface 1022 having a convex lateral curvature axis 1024. Grasping surface 1022 terminates in outer lateral edges 1026. In alternative embodiments, edges 1026 may be omitted, as surface 1022 may have a smoothed transition to surface 1014. The lateral curvature of surface 1022 is formed, in accordance with the present invention, to match or closely approximate the curvature of a sectional matrix band or other desired dental appliance. In alternative embodiments, angulations may be implemented in place of curvature or curvature may be omitted altogether.

As depicted in FIGS. 10a–10c, surface 1022 further comprises some longitudinal curvature, orthogonal to axis 1024, to match or closely approximate the curvature of a sectional matrix band or other desired dental appliance. In other embodiments, the longitudinal axis of surface 1022 may be substantially straight, or may comprise some angulation to match or closely approximate the curvature of a sectional matrix band or other desired dental appliance. Thus, surface 1022 may be formed in resemblance to a number of contour profiles (e.g., quasi-spherical, egg-shaped, quasi-conical, quasi-cylindrical, etc.).

Member 1008 is formed having an outer surface 1028 and various inner surface features. Member 1008 terminates in a mating feature 1030, formed or adapted to engage with member 1006 in accordance with the present invention. The particular form factor or shape of feature 1030 may vary depending upon the contour of surface 1022. As depicted in FIG. 10b, feature 1030 comprises a saddle-shaped member, comprising a transition feature 1032 and a grasping surface 1034.

Feature 1032 is formed, in accordance with the present invention, to provide secure engagement in cooperation with feature 1016 as described in greater detail hereafter. Feature 1032 may comprise a ridge, shelf or other contrivance, and provides a transition from, and demarcation between, region 1012 and surface 1034.

Grasping surface 1034 has a concave lateral curvature, formed to complement the curvature axis 1024 of surface 1022, in accordance with the present invention. The lateral curvature of surface 1034 is formed, in accordance with the present invention, to match or closely approximate the curvature of a sectional matrix band or other desired dental appliance. In alternative embodiments, angulations may be implemented in place of curvature or curvature may be omitted altogether. As depicted in FIGS. 10a–10c, surface 1034 further comprises some longitudinal curvature, to match or closely approximate the curvature of a sectional matrix band or other desired dental appliance. In other embodiments, the longitudinal axis of surface 1034 may be substantially straight, or may comprise some angulation in accordance with the present invention. Furthermore, feature 1030 may comprise outside flange portions 1036, laterally extending surface 1034 to provide greater lateral support and grasp of a sectional matrix band held within instrument 1000. In alternative embodiments, however, feature 1030 may be formed having any other suitable topology (e.g., quasi-cylindrical).

Although the specific embodiments of constituent members may vary slightly, apparatus 1000 is generally formed and operable to render members 1006 and 1008 in pressure-fit, engagable relation to one another while grasping a sectional matrix band between surfaces 1022 and 1034. The orientations, curvatures, or angulations of members 1002, 1004, 1006, 1008, 1010, 1012, 1016, 1018, 1020, 1022, 1026, 1030, 1032, 1034 and 1036 are, in this embodiment, formed to facilitate the placement or manipulation of a sectional matrix band in a mesial orientation.

As actuating members 1002 and 1004 are brought together, grasping area 1020 is brought longitudinally into feature 1030, in a partially sleeved relationship with surface 1034. Depending upon a user's preference, a sectional matrix band may be positioned in instrument 1000 prior to, or just as, area 1020 initiates contact with member 1008.

As further pressure is applied to members 1002 and 1004, feature 1030 slides longitudinally along surface 1022 until feature 1032 enters recess 1018 and comes to rest against feature 1016. Surfaces 1022 and 1034 thus come into pressure fit contact with one another, holding the sectional matrix band stably and securely therebetween. The matrix band is further stabilized and secured, along its upper edge, against feature 1016.

In alternative embodiments, increased grasping pressure may be induced between members 1006 and 1008 utilizing some locking or fulcrum mechanism in accordance with the present invention, as previously described.

Figure 11:
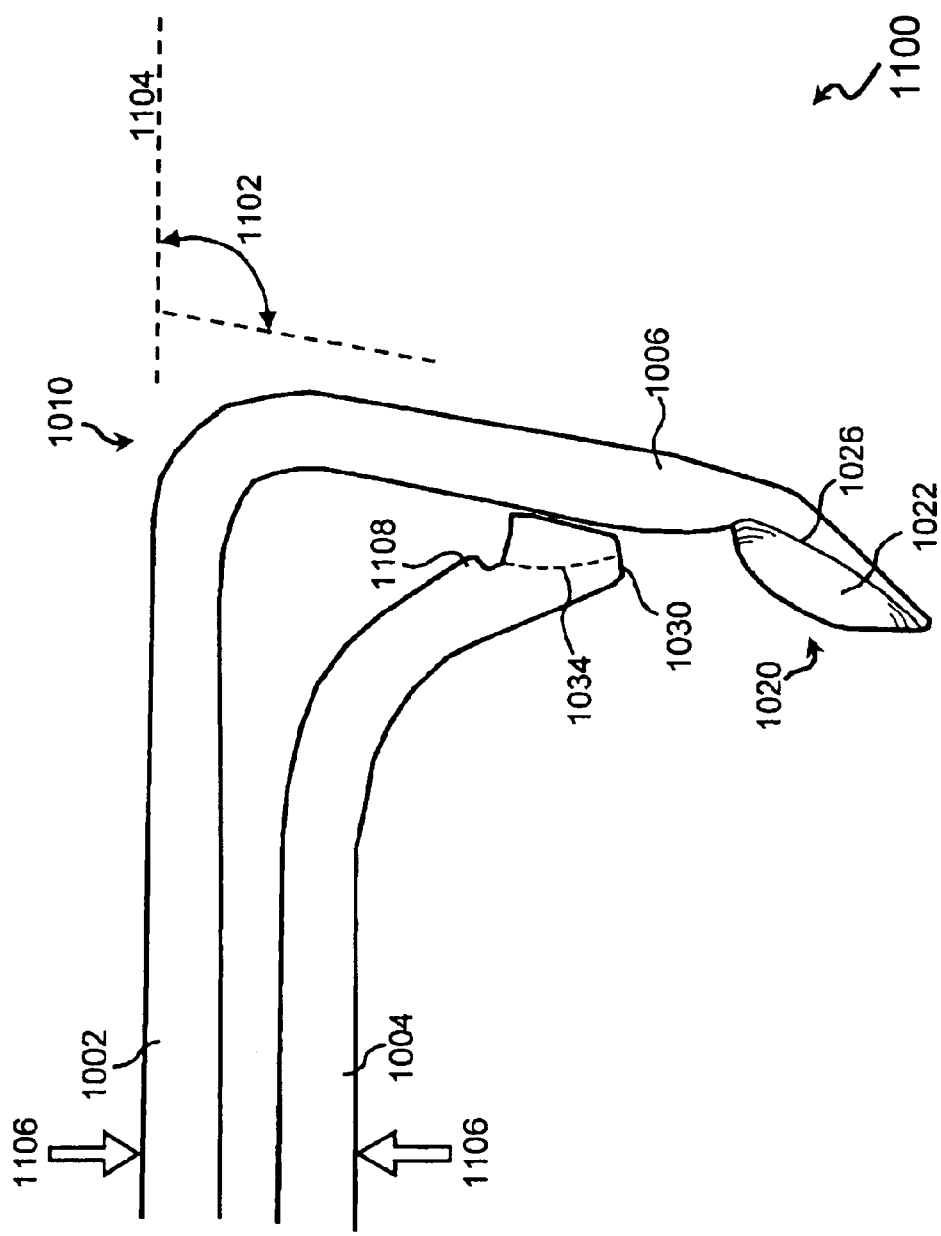
FIG. 11 illustrates another embodiment of an instrument according to the present invention.

Referring now to FIG. 11, a portion of an instrument 1100 is depicted. Instrument 1100 represents one alternative embodiment of instrument 1000, particularly biased for mesial orientation. With certain exceptions described below, constituent members of instrument 1100 are generally identical to those of instrument 1000. For instrument 1100, transition area 1010 is angled or curved inward to such an extent that member 1006 forms an angle 1102 with the plane 1104 of member 1002 that is greater than 90 degrees. Further bias for mesial orientation may optionally be provided by inwardly angling or curving grasping area 1020 with respect to the rest of member 1006. This orientation provides a more optimal mesial bias for instrument 1100. Depending upon the actuating assembly used, however, this orientation may require a reconfiguration of some features and of the functional and spatial relationship between actuating members 1002 and 1004.

Referring back to FIGS. 10a–10c, member 1006 forms an angle of less than or equal to 90 degrees with respect to the plane of member 1002. With the configuration of instrument 1000, members 1006 and 1008 are separated in a nearly-vertical spaced apart relationship in the absence of pressure to members 1002 and 1004. As closing pressure 1040 is applied to force members 1002 and 1004 together, member 1008 is effectively brought "up" into pressure-fit contact with member 1006 as previously described. Thus, instrument 1000 is "open" when no pressure 1040 is applied.

In contrast, the greater mesial bias of instrument 1100 renders such relationship physically impossible for many actuating apparatus. Instrument 1100 therefore alters the the functional and spatial relationship of actuating members 1002 and 1004 to render them "open" when pressure 1106 is applied, and "closed" in the absence of pressure 1106.

In instrument 1100, member 1008 is formed having an apical seating feature 1108. Feature 1108 may comprise a ridge, shelf or other contrivance in accordance with the present invention. Feature 1108 may protrude slightly from the inner surface of member 1008, or may be flush or contoured therewith. Feature 1108 adjoins the upper perimeter of mating feature 1030.

Again, grasping area 1020 is formed with a grasping surface 1022 having a convex lateral curvature axis. Grasping surface 1022 may terminate in outer lateral edges 1026. The lateral curvature of surface 1022 is formed, in accordance with the present invention, to match or closely approximate the curvature of a sectional matrix band or other desired dental appliance. In alternative embodiments, angulations may be implemented in place of curvature or curvature may be omitted altogether.

As depicted in FIG. 11, surface 1022 further comprises some longitudinal curvature, to match or closely approximate the curvature of a sectional matrix band or other desired dental appliance. In other embodiments, the longitudinal axis of surface 1022 may be substantially straight, or may comprise some angulation to match or closely approximate the curvature of a sectional matrix band or other desired dental appliance. Again, surface 1022 may be formed in resemblance to a number of contour profiles (e.g., quasi-spherical, egg-shaped, quasi-conical, quasi-cylindrical, etc.).

Member 1008 terminates in a mating feature 1030, formed or adapted to engage with member 1006 in accordance with the present invention. The particular form factor or shape of feature 1030 may vary depending upon the contour of surface 1022. As depicted in FIG. 11, feature 1030 comprises a saddle-shaped member with grasping surface 1034.

Grasping surface 1034 has a concave lateral curvature, formed to complement the curvature axis of surface 1022, in accordance with the present invention. The lateral curvature of surface 1034 is formed, in accordance with the present invention, to match or closely approximate the curvature of a sectional matrix band or other desired dental appliance. In alternative embodiments, angulations may be implemented in place of curvature, or curvature may be omitted altogether. As depicted in FIG. 11, surface 1034 further comprises some longitudinal curvature, to match or closely approximate the curvature of a sectional matrix band or other desired dental appliance. In other embodiments, the longitudinal axis of surface 1034 may be substantially straight, or may comprise some angulation in accordance with the present invention. Feature 1030 may comprise outside flange portions, or may be formed having any other suitable topology (e.g., quasi-cylindrical).

Although the specific embodiments of constituent members may vary slightly, apparatus 1100 is generally formed and operable to render members 1006 and 1008 in pressure-fit, engagable relation to one another while grasping a sectional matrix band between surfaces 1022 and 1034. The orientations, curvatures, or angulations of member are, as previously noted, formed to particularly bias the instrument in a mesial orientation.

In the presence of actuating pressure 1106, actuating members 1002 and 1004 are brought together, "opening" and disengaging members 1006 and 1008. When "opened", member 1008 separates from member 1006 in a nearly-vertical spaced apart relationship, where member 1008 is above member 1006. The inner surface of member 1008 may rest in contact with the inner surface of member 1006, or it may be slightly spaced apart therefrom. During operation of instrument 1100, either or both members 1006 and 1008 may deform slightly to allow closure in accordance with the present description. As opening pressure 1106 is decreased, separating members 1002 and 1004, member 1008 is forced "down" into pressure-fit contact with member 1006.

Thus, instrument 1100 is "open" when pressure 1106 is applied. As actuating members 1002 and 1004 are released, grasping area 1020 is brought longitudinally into feature 1030, in a partially sleeved relationship with surface 1034. Depending upon a user's preference, a sectional matrix band may be positioned in instrument 1000 prior to, or just as, area 1020 initiates contact with member 1008. As pressure 1106 is completely eliminated, feature 1030 slides longitudinally along surface 1022 until it comes to rest, in full pressure fit contact with surface 1022, holding the sectional matrix band stably and securely therebetween. The matrix band is further stabilized and secured, along its upper edge, against feature 1016.

In alternative embodiments, increased grasping pressure may be induced between members 1006 and 1008 utilizing some locking or fulcrum mechanism in accordance with the present invention, as previously described.

For all embodiments, selection of materials for formation of the assemblies will depend on a number of factors. In all cases, materials selected must be durable enough to withstand the pressures (e.g., grasping, closing, pulling) applied throughout the system during a procedure. Furthermore, the materials utilized should be malleable enough to be formed into the desired shapes and orientations. If an embodiment requires a deformable member, the material used to form that member should be flexible enough to provide the desired deformation while remaining durable enough to withstand the pressures applied.

If an assembly or a sub-portion thereof is intended to be of a disposable, one-use nature, then a reliable but inexpensive material (e.g., plastic) may be used in production. If an assembly or a member is intended to be of a re-usable nature, then a durable material (e.g., stainless steel), capable of withstanding repeated sterilization procedures, may be used in production.

The embodiments and examples set forth herein are presented to best explain the present invention and its practical application and to thereby enable those skilled in the art to make and utilize the invention. However, those skilled in the art will recognize that the foregoing description and examples have been presented for the purpose of illustration and example only. The description as set forth is not intended to be exhaustive or to limit the invention to the precise form disclosed. Many modifications and variations are possible in light of the above teaching without departing from the spirit and scope of the following claims.

What is claimed is:

1. A dental instrument biased toward a mesial or distal orientation, the instrument comprising:
    an actuating assembly having first and second actuating members;
    a first grasping member, coupled to the first actuating member at a first transition area, having a first grasping surface formed, proximate to the first transition area, with a first contour; and
    a second grasping member, coupled to the second actuating member at a second transition area, having a second grasping surface formed, proximate to the second transition area, with a second contour.

2. The instrument of claim 1, wherein the instrument is biased exclusively toward a mesial orientation.

3. The instrument of claim 2, wherein the first and second contours comprise a lateral curvature.

4. The instrument of claim 2, wherein the first and second contours comprise a longitudinal curvature.

5. The instrument of claim 2, wherein the first and second contours comprise a lateral angulation.

6. The instrument of claim 2, wherein the first and second contours comprise a longitudinal angulation.

7. The instrument of claim 1, wherein the instrument is biased exclusively toward a distal orientation.

8. The instrument of claim 7, wherein the first and second contours comprise a lateral curvature.

9. The instrument of claim 7, wherein the first and second contours comprise a longitudinal curvature.

10. The instrument of claim 7, wherein the first and second contours comprise a lateral angulation.

11. The instrument of claim 7, wherein the first and second contours comprise a longitudinal angulation.

12. The instrument of claim 1, wherein the actuating assembly comprises a bifurcated assembly.

13. The instrument of claim 1, wherein the actuating assembly comprises a stylus assembly.

14. An instrument for mesial manipulation of a matrix band, comprising:
    an actuating assembly, having first and second actuating members;
    a first grasping member, coupled to the first actuating member at a first transition area, having a convex grasping surface formed proximal to the first transition area;
    a second grasping member, coupled to the second actuating member at a second transition area, having an apical seating feature formed proximal to the second transition area, having a concave grasping surface formed proximal to the apical seating feature;
    wherein the actuating assembly is operable to engage the convex and concave grasping surfaces in a pressure fit relationship.

15. An instrument for distal manipulation of a matrix band, comprising:
    an actuating assembly, having first and second actuating members;
    a first grasping member, coupled to the first actuating member at a first transition area, having an apical seating feature formed proximal to the first transition area and having a concave grasping surface formed proximal to the apical seating feature;
    a second grasping member, coupled to the second actuating member at a second transition area, having a mating feature formed proximal to the second transition area and having a convex grasping surface formed proximal to the mating feature;
    wherein the actuating assembly is operable to engage the convex and concave grasping surfaces in a pressure fit relationship.

* * * * *